United States Patent
Utas et al.

(10) Patent No.: US 10,960,175 B2
(45) Date of Patent: Mar. 30, 2021

(54) STEAM STERILIZED CATHETER ASSEMBLY

(71) Applicant: DENTSPLY IH AB, Mölndal (SE)

(72) Inventors: Jan Utas, Kungsbacka (SE); Anna Hedegärd, Mölndal (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

(21) Appl. No.: 16/022,406

(22) Filed: Jun. 28, 2018

(65) Prior Publication Data
US 2019/0001098 A1 Jan. 3, 2019

(30) Foreign Application Priority Data

Jun. 30, 2017 (EP) .................................... 17178962

(51) Int. Cl.
*A61M 25/00* (2006.01)
*A61M 27/00* (2006.01)
*A61L 2/07* (2006.01)
*B65B 55/18* (2006.01)

(52) U.S. Cl.
CPC .............. *A61M 25/002* (2013.01); *A61L 2/07* (2013.01); *A61L 2202/24* (2013.01); *A61M 25/0017* (2013.01); *A61M 27/00* (2013.01); *A61M 2025/0046* (2013.01); *A61M 2210/1085* (2013.01); *B65B 55/18* (2013.01)

(58) Field of Classification Search
CPC ............ A61M 25/002; A61M 25/0017; A61M 2025/0046; A61M 2210/1085; A61M 27/00; A61L 2/07; A61L 2202/24; B65B 55/18

USPC ......................... 206/210, 364, 438, 205, 207
See application file for complete search history.

(56) References Cited

U.S. PATENT DOCUMENTS

| 3,967,728 A | 7/1976 | Gordon et al. |
|---|---|---|
| 4,269,310 A | 5/1981 | Uson |
| 6,848,574 B1 | 2/2005 | Israelsson et al. |

(Continued)

FOREIGN PATENT DOCUMENTS

| DE | 102007021118 | 11/2008 |
|---|---|---|
| EP | 0093093 | 11/1983 |

(Continued)

OTHER PUBLICATIONS

European Search Report for European Patent Application No. 17178962.1, dated Dec. 19, 2017 (8 pages).

*Primary Examiner* — Chun Hoi Cheung
(74) *Attorney, Agent, or Firm* — Perkins Coie LLP (57) ABSTRACT

A sterilized medical device assembly comprises a medical device having a hydrophilic surface on at least a part thereof, such as a hydrophilic urinary catheter, and a package forming a closed compartment accommodating the medical device. The medical device is arranged in an activated state in the package, with the hydrophilic surface being wetted with a wetting fluid. In addition, a small amount of wetting liquid is freely arranged in the closed compartment of the package, and in direct contact with the hydrophilic surface of the medical device. The volume of the wetting liquid corresponds to between 0.01% and 10% of a volume of the closed compartment. The medical device assembly is steam sterilized, and it has been found that the extra small amount of free liquid is very efficient in ensuring a reliable and efficient steam sterilization.

22 Claims, 3 Drawing Sheets

(56) References Cited

U.S. PATENT DOCUMENTS

| | | | |
|---|---|---|---|
| 7,380,658 B2* | 6/2008 | Murray | A61M 25/0009 |
| | | | 206/364 |
| 7,766,163 B2* | 8/2010 | Tanghoej | A61M 25/002 |
| | | | 206/210 |
| 9,925,352 B2* | 3/2018 | McBurney | B65B 55/08 |
| 2005/0043715 A1* | 2/2005 | Nestenborg | A61M 25/002 |
| | | | 604/544 |
| 2006/0163097 A1* | 7/2006 | Murray | A61M 25/0009 |
| | | | 206/364 |
| 2011/0114520 A1* | 5/2011 | Matthison-Hansen | |
| | | | A61M 25/002 |
| | | | 206/364 |
| 2014/0360896 A1* | 12/2014 | Torstensen | A61M 25/002 |
| | | | 206/210 |
| 2015/0068927 A1* | 3/2015 | McBurney | B65B 55/08 |
| | | | 206/210 |
| 2015/0265801 A1* | 9/2015 | Rostami | A61L 31/048 |
| | | | 604/544 |

FOREIGN PATENT DOCUMENTS

| | | |
|---|---|---|
| EP | 0217771 | 4/1984 |
| EP | 3311872 | 4/2018 |
| JP | 2000281144 | 10/2000 |

* cited by examiner

STEAM STERILIZED CATHETER ASSEMBLY

CROSS REFERENCE TO RELATED APPLICATIONS

This patent document claims the benefits and priority to European Patent Convention Application No. 17178962.1, filed on Jun. 30, 2017, which is incorporated herein by reference in its entirety.

FIELD OF THE INVENTION

The present disclosure relates to a medical device assembly comprising a medical device, which is steam sterilized. Specifically, the disclosed embodiments pertain to a medical device having a hydrophilic surface, wherein the hydrophilic surface is wetted during storage. The disclosed embodiments are particularly related to catheters, and specifically to urinary catheters.

BACKGROUND

The present disclosure relates to a medical device assembly, and in particular for urinary hydrophilic catheters. Catheters are commonly used for draining bodily fluids, e.g. from the bladder. Urinary catheters can be of an indwelling type, for long term use, such as days or even weeks, or for intermittent use, whereby the catheters are used for a single draining procedure, typically lasting a few minutes. Intermittent urinary catheters are e.g. used by a large group of persons for self-catheterization, which is a daily-life procedure, taking place several times a day. Typically, catheters for intermittent catheterization are used by patients suffering from urinary retention, due to e. g. spinal cord injury, Multiple Sclerosis or Prosthatic Hyperplasia. Using an intermittent catheter, the bladder may be drained through a natural or artificial urinary canal. Many catheters, such as those for intermittent catheterization, are provided with a hydrophilic coating or the like, providing a smooth and slippery surface when wetted, for safe and comfortable insertion in the urinary canal.

Many hydrophilic catheter assemblies include a supply of wetting fluid, either in direct contact with the catheter or in a separate compartment, for clean and convenient activation of the hydrophilic surface before use.

It is important that the packaging used for catheters having friction-reducing surface coatings have properties and features that provide the catheter with a long shelf-life because the time that a urinary catheter is held in storage prior to use can be rather lengthy. To this end, the catheter packaging needs to ensure that the friction-reducing coating on the catheter is protected, for instance against the environment. The catheter assembly also, typically, needs to be sterilized soon after assembly, and needs to maintain the sterile state of the catheter during storage. A typical sterilizing process for hydrophilic urinary catheters involves exposing the catheter to ethylene oxide gas or radiation.

Ethylene oxide sterilization is a relatively cost-efficient sterilization method. For catheter assemblies where the catheter is maintained in a dry state during storage, ethylene oxide sterilization may be used. However, in order to work properly, the package then needs to be gas permeable. This lowers the shelf life of the product, and may inter alia lead to ingress of moisture into the package, which may deteriorate the hydrophilic surface of the catheter. Further, there is also a risk of ethylene oxide residue being left in the package. Further, in assemblies where the catheter is maintained in wetted state, ethylene oxide is generally not useable, since ethylene oxide will then leave unwanted residues in the wetting liquid.

Radiation sterilization requires complex and costly radiation sterilization equipment, which makes production costly and complex. Further, the radiation often affects the properties of the catheter material, and leads to cross-linking and other effects which may deteriorate the product.

Further, it has been proposed in U.S. Pat. No. 6,848,574 to use steam sterilization for sterilization of hydrophilic urinary catheter assemblies which are maintained in a wetted, ready-to-use state. However, for steam sterilization to work, the package needs to be completely filled with wetting liquid, such as water. This makes the product relatively heavy, and complex to produce. It also leads to a great risk of spilling the wetting liquid upon opening of the package.

Thus, there is still a need for improved medical device assemblies for hydrophilic medical devices, such as hydrophilic urinary catheters, and in particular for assemblies where the medical device is maintained in an activated, wetted state. In particular, there is a need for such assemblies which can be produced more cost-efficiently, and in which the problems related to sterilization can be alleviated. The assembly/package should also preferably be rather small, so that it can easily be carried around by the user in his/her daily life.

SUMMARY

It is therefore an object of the disclosed embodiments to provide a medical device assembly which at least alleviates the above-discussed problems. This object is obtained by means of a medical device assembly and a method in accordance with the appended claims.

According to a first aspect of the disclosed embodiments there is provided a sterilized medical device assembly comprising:

a medical device having a hydrophilic surface on at least a part thereof;

a package forming a closed compartment accommodating said medical device, wherein said medical device is arranged in an activated state in said package with said hydrophilic surface being wetted with a wetting fluid; and a wetting liquid being freely arranged in said closed compartment of the package, and in direct contact with said hydrophilic surface of the medical device;

wherein a volume of said wetting liquid corresponds to between 0.01% and 10% of a volume of said closed compartment, and wherein said medical device assembly is steam sterilized.

The phrase "arranged in an activated state in said package" is meant to convey that the hydrophilic surface is in a wetted state when enclosed in the sealed package in a storage state. This wetted state may be present immediately following closing and sealing of the package, or be obtained after some time of storage. The activated state may thus be provided by pre-wetting of the catheter, prior to arrangement of the catheter in the package, but may alternatively be provided after placement of the catheter in the package. Specifically, wetting of the hydrophilic surface may occur during a period of storage in a sealed container by provision of a humid atmosphere in the package, as is known in the art.

It has now been found that despite the prejudice in the art, as e.g. shown in U.S. Pat. No. 6,848,574 discussed above, it is in fact possible to use steam sterilization for pre-wetted medical device assemblies. In tests conducted by the inventors, which are discussed in more detail in the following, it has been shown that pre-wetted catheters arranged in a sealed package but without an additional supply of wetting liquid in the package cannot be steam sterilized. However, surprisingly, it was found that only an extremely limited volume of additional wetting liquid is sufficient to make steam sterilization possible.

The small amount of additional wetting liquid does not add significantly to the weight of the product, and also there is almost no risk of spillage when the package is opened, since there is only a small amount of wetting liquid at the bottom of the package.

Further, it is believed that the small amount of additional wetting liquid over time creates a humid atmosphere in the package, and preferably a saturated humid atmosphere, which serves to maintain the wetted state of the pre-wetted hydrophilic surface of the medical device. Hereby, the longevity of the product is improved, so that the product can be stored for a longer time period prior to use without becoming dry. Thus, the shelf life of the product can be in the range of 3-5 years, or even longer.

Since the hydrophilic surface is maintained in a wetted state during storage, the medical device is immediately ready-to-use upon removal from the package, and need not be wetted or treated in any way prior to use.

The hydrophilic surface may be arranged as a hydrophilic coating arranged on a substrate of the medical device, as is per se well known in the art. However, the hydrophilic surface may alternatively be arranged as an integrated part of the medical device, such as an integrated layer, or alternatively, the entire medical device, or part(s) of the medical device, may be made of a hydrophilic material. The hydrophilic surface is preferably arranged to provide low friction when wetted.

In some embodiments, the medical device has a shaft for insertion into a body cavity or body passageway which presents the hydrophilic surface, on an exterior surface thereof. Examples of such medical devices are catheters such as urinary catheters for bladder drainage. The hydrophilic surface may be a surface provided with a hydrophilic coating, for example made in accordance with EP 0 093 093 and EP 0 217 771, which are incorporated by reference herein. The wetting liquid may be an aqueous solution.

The hydrophilic coating preferably forms a polyurea network, and most preferably the polyurea network is arranged to form a covalent bond to active hydrogen groups in the substrate. Alternatively, the hydrophilic coating may form an ester bond or an epoxy bond to active hydrogen groups in the substrate.

According to one embodiment, coating of the substrate material may be made by a process comprising the steps of: applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature. However, other hydrophilic coatings are also feasible, such as a coating comprising hydrophilic polymers cross-linked directly to the substrate. The cross-linking may be effected by means of irradiation, e.g. by electron beams or UV light.

As already discussed, steam sterilization is highly advantageous. Hereby, the entire medical device assembly, including both the medical device and the wetting liquid, could be sterilised at the same time, which render the sterilisation process fast and effective.

The steam-sterilization technique is preferred, since it has the advantage over ethylene oxide gas and β- or γ-radiation sterilization that there is no formation or absorption of harmful reaction products in the wetting liquid, in the medical device material or in the hydrophilic surface.

More specifically, a problem with using ethylene oxide sterilization is that an amount of residual ethylene oxide or degradation products are absorbed by the wetting liquid or the medical device, which could be harmful for the user of the medical device. Further, ethylene oxide could only be used for sterilizing the medical device, where after the medical device and sterile wetting liquid must be aseptically packaged. However, the provision of such an aseptic environment for the packaging is both expensive and difficult to achieve in practice. Those problems with the ethylene oxide sterilization could be overcome by using steam-sterilization instead.

Further, a problem with β- or γ-radiation sterilization is that harmful reaction products might be produced in the medical device. The radiation also starts a degradation process in the material of the medical device, which is typically a plastic material or the like, whereby the shelf-life is shortened. Still further, the medical device has to be sterilized either before it is placed in the package together with the wetting liquid or within a short period thereafter. The pre-sterilization of the medical device is not preferred, since it requires an aseptic packaging environment, as is discussed above. If a non-sterilized object is placed in a sterilized liquid the liquid is pre-contaminated, and the pre-contamination increases over the time. If the pre-contamination becomes too large, the sterilization process will not be able to sufficiently sterilize the product. Further, a too large pre-contamination gives rise to high, and possibly harmful endotoxin levels. However, it may be difficult to perform the radiation sterilization within a prescribed time period, since radiation sterilisation equipment is large and expensive, and it not realistic to have such an equipment on each packaging facility. However, steam-sterilization equipment, such as commercially available autoclaves, is much less expensive. Hence, all the referred problems with radiation sterilization could be overcome by using steam-sterilization instead.

Further, steam sterilization equipment does not require any special buildings or the like, but can be used in any type of building. Such equipment is also relatively small and low in cost, thereby making it possible to use it for example at small production facilities etc. Steam sterilization is also a relatively fast procedure, and is environmentally friendly.

The steam sterilization is preferably made with an adjustable external counter-pressure, as is per se known in the art for steam sterilization of closed containers. Hereby, the effect of the overpressure which forms inside as the temperature rises is neutralized. Otherwise, the overpressure may cause a burst or even an explosion of the container if the container does not have sufficient strength to withstand this pressure. However, by using an external counter-pressure, the strain on the container is significantly reduced, which makes it possible to steam-sterilize packages with thin walls etc. Counter-pressure autoclaves may operate in various ways, and may be of different types, as is per se known in the art. For example, the counter-pressure autoclave may be a superheated water spray autoclave or a steam and air mixture autoclave.

The steam sterilization may e.g. be performed at about 121 deg. C., and be performed during a time period of about 20 minutes. A counter-pressure may e.g. be continuously adjusted to be about 1 bar from the start, at room temperature, about 1.1 bar at 50 deg. C., about 2.0 bar at 100 deg. C. and about 3.0 bar at 121 deg. C.

However, steam sterilization may also be performed at higher or lower temperatures. Typically, steam sterilization at lower temperatures would be performed during longer time periods, whereas steam sterilization at higher temperatures may be performed during shorter time periods. Thus, depending on e.g. the temperatures the various parts of the assembly are able to withstand without degradation, a suitable sterilization temperature may be selected, and the time period for the sterilization may be selected in dependence on the temperature.

Generally, it is preferable that all parts of the assembly, and in particular the medical device and the package, are capable of enduring a temperature of at least 100 deg. C. without degradation, and preferably at least 120 deg. C., and most preferably at least 130 deg. C. To this end, the materials of these parts preferably have melting temperatures exceeding such temperature limits. Such suitable materials may be polyurethanes, polyether block amides, polyesters, silicon rubber, elastomeric alloys such as Santoprene® and polyolefin alloys based on polypropylene or SEBS (Styrene Ethylene Butadiene Styrene). An example of a polyether block amide that could be used for forming the medical device is Pebax® (Elf Atochem S.A.).

Thus, the package is preferably made of one or several material(s) having a melting temperature exceeding 120 deg. C., and preferably exceeding 130 deg. C., whereby the package can endure temperatures of 120 deg. C. or more without significant deformation or deterioration.

Further, the medical device is preferably made of one or several material(s) having a melting temperature exceeding 120 deg. C., and preferably exceeding 130 deg. C., whereby the medical device can endure temperatures of 120 deg. C. or more without significant deformation or deterioration.

In case a combination of several materials are used for forming the package and/or the medical device, the material having the lowest melting temperature is normally the one setting the overall melting temperature for the combination.

The additional wetting liquid, i.e. the wetting liquid being freely arranged in the closed compartment of the package, and in direct contact with the hydrophilic surface of the medical device, has a volume corresponding to between 0.01% and 10% of an internal volume of the closed compartment. Preferably, the volume of the wetting liquid corresponds to between 0.1% and 5% of the internal volume of the closed compartment.

A conventional package for a hydrophilic urinary catheter may have an internal volume of about 100 ml. Thus, differently put, the volume of the wetting liquid is preferably in the range 0.1-5 ml, and preferably in the range 0.1-3 ml, such as 0.01 ml, 0.05 ml, 0.1 ml, 0.2 ml, 0.3 ml, 0.5 ml, 1 ml, 2 ml or 3 ml.

A conventional hydrophilic urinary catheter may e.g. contain 10 □l water/cm2 when wetted. Thus, a male catheter, which is typically 30-40 cm long, may contain about 300 □l when wetted. Thus, the small additional supply of wetting liquid preferably has a volume of the same order as the volume of wetting liquid contained in the pre-wetted medical device, such as in the range of 1-10 times the volume contained in the medical device, and preferably in the range of 1-5 times, and most preferably in the range of 1-3 times.

It is assumed that 1 µl water per ml package volume can be sufficient for obtaining a sufficiently humid atmosphere in the package to render steam sterilization possible, since the volume of water vapor at 1 bar is about 1000 times the corresponding volume of liquid water. However, this may vary slightly depending on ambient pressure, temperature, etc. Further, some variations during manufacturing may be expected. Thus, to be certain that the desired effect is obtained, it is assumed that a lower limit for the volume of the additional wetting liquid in real life embodiments would be 0.1% of the internal volume of the compartment/package.

In the foregoing, reference has been made to the internal volume of the compartment/package. However, to be correct, this internal volume is the nominal internal volume of the package, but reduced with the volume of the medical device, i.e. the available, free volume in the package when it also contains a medical device. However, since the nominal volume of a typical urinary catheter package would be about 100 ml, and the volume of a typical urinary catheter would be about 4 ml, we may, in real life applications, in most cases consider the nominal volume of the package to be the internal volume, since the effect of the catheter volume is close to negligible.

The package is preferably impermeable to the wetting liquid, and preferably made of a gas impermeable material. This ensures that moisture does not penetrate out from the package during storage, and enhances the shelf-life of the product.

However, the package may alternatively be an inner package enclosed in an additional outer package. In this case, the inner package need not be of a construction which is totally impermeable to the wetting liquid if the outer package also has good impermeability to the wetting liquid. The inner package could in this instance e.g. be made from polyurethane or polypropylene. In case both an inner and an outer package are used, the outer package may enclose a plurality of inner packages, each inner package enclosing one or more medical devices.

The (inner) package may be made of a sheet material, and preferably a foil sheet material. The sheet(s) may be formed by a weldable material. However, preferably the sheet(s) comprise laminated sheet(s), having a weldable inner layer and a protective outer layer. The package may e.g. be made of two sheets being connected around the edges, e.g. by welding, or by a single sheet being folded, and connected around the open edges (whereby one edge connection is formed by the fold). For example, the laminated sheet may be an aluminum laminate, e.g. formed as PET/Al/PP or PA/Al/PP. The sheet material is also preferably a flexible material.

However, the impermeable layer may also be made of other materials than aluminum. For example one or several of the following gas impermeable materials could be used: aluminum foil laminate, poly(vinylidene chloride) or laminate comprising a metallised film, such as metallised poly (ethylene terepthalate), or silicon oxide coated film, or a laminate comprising aluminum oxide.

The medical device is preferably a catheter, and preferably a urinary catheter, and most preferably a urinary catheter for intermittent, short time use. The term "short term use" indicates a use that is limited in time, and in particular limited to a time period of less than 15 minutes, and preferably less than 10 minutes, and most preferably less than 5 minutes.

However, the present disclosure is also useful for many other types of medical devices having a hydrophilic coating or a hydrophilic surface. Accordingly, the present disclosure is not limited to urinary catheters. Examples of such other medical devices for which the present disclosure is useful are vascular catheters and other types of catheters, endo and laryngoscopes, tubes for feeding, or drainage or endotracheal use, condoms, wound dressings, contact lenses, implants, extracorporeal blood conduits, membranes e.g. for dialysis, blood filters and devices for circulatory assistance.

The wetting liquid is preferably an aqueous liquid, comprising at least 75% of weight of water, and preferably at least 80% of weight, and more preferably at least 85% of weight, and most preferably at least 90% of weight. In some embodiments, the wetting liquid may be plain water. However, the wetting liquid may also comprise one or more additives, such as an anti-bacterial agent, a pharmaceutical active substance, or the like.

One or several osmolality increasing agent(s), such as sodium chloride, may also be provided. The osmolality increasing agent(s) may be provided in the wetting liquid, but may additionally or alternatively be provided in the hydrophilic surface, such as being integrated in a hydrophilic coating. In case one or several osmolality increasing agents are dissolved in the wetting liquid, the wetting fluid preferably comprises total concentration of the dissolved osmolality-increasing compound(s) exceeding 300 mOsm/dm3, and preferably exceeding 600 mOsm/dm3, and preferably in the range of 300-1500 mOsm/dm3, and more preferably 600-1500 mOsm/dm3, and most preferably in the range of 800-1000 mOsm/dm3. The unit milliosmole (mOsm), i.e. one-thousandth of an osmole, represents the amount of substance that dissolves in a solvent to form one mole of osmotically active units (atoms, ions, etc), e.g., 1 mole of glucose, which is not ionizable, forms 1 osmole of solute, but 1 mole of sodium chloride forms 2 osmoles of solute. This very high concentration of osmolality-increasing compound, exceeding 600 mOsm/dm3, in the wetting liquid is in line with the normal saline concentration in urine (which is about 900 mOsm/dm3) and is much higher than the concentration in a physiological saline solution (about 290 mOsm/dm3). Such a high concentration improves the properties of the resulting wetted hydrophilic layer in respect of e.g. stability during wetting, and thereby stability during use, friction, and in particular a lowered extraction force, and water retention.

The osmolality-increasing compound(s) is/are preferably selected from the group consisting of urea, amino acids, mono and disaccharides, sugar alcohols, and non-toxic organic and inorganic salts or acids, polypeptides, diols, triols, low molecular polyols, alcohols and mixtures thereof.

Most preferably, the osmolality-increasing compound(s) is selected from the group consisting of glucose, glycerol, sorbitol, sodium chloride, sodium citrate, sodium benzoate, calcium chloride, potassium chloride, potassium iodide and potassium nitrate.

In particular, it is preferred to use sodium chloride. If only sodium chloride is used as an osmolality increasing agent, it is preferred to use 2-4% of weight of sodium chloride in the wetting liquid, and most preferably 2.5-3.5% by weight.

The catheter may comprise a substrate and a hydrophilic coating, wherein the substrate comprises, or is of, one or several material(s) from the group polyurethanes, polyether block amides, silicon rubber, elastomeric alloys such as Santoprene® and polyolefin alloys based on polypropylene or SEBS (Styrene Ethylene Butadiene Styrene), and mixtures thereof.

According to another aspect of the disclosed embodiments, there is provided a method for producing a sterilized medical device assembly comprising the steps:

providing a medical device having a hydrophilic surface on at least a part thereof;

wetting the hydrophilic surface of the medical device with a wetting fluid;

accommodating the medical device in a closed and sealed compartment of a package together with a wetting liquid being freely arranged in the closed compartment and in direct contact with said hydrophilic surface of the medical device, wherein a volume of said wetting liquid corresponds to between 0.01% and 10% of a volume of said closed compartment; and steam sterilizing said medical device assembly.

As discussed in the foregoing, the steam sterilization is preferably a counter-pressure sterilization, whereby the pressure in an autoclave is controlled in dependence of the temperature.

These and other aspects of the disclosed technology will be apparent from and elucidated with reference to the embodiments described hereinafter.

BRIEF DESCRIPTION OF THE DRAWINGS

For exemplifying purposes, the disclosed embodiments will be described in closer detail in the following with reference to embodiments thereof illustrated in the attached drawings, wherein.

DETAILED DESCRIPTION OF PREFERRED EMBODIMENTS

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the medical device, etc.

The medical device assembly can be used for many types of medical devices. However, it is particularly suited for catheters. Catheters may be used for many different purposes, and for insertion into various types of body-cavities. However, the following discussion is in particular concerned with the preferred field of use, hydrophilic urinary catheters, even though the invention is not limited to this particular type of catheters, and also not to catheters.

The specific package, and the specific opening arrangements provided in this package, which will be discussed in the following are described in the published patent application no. EP 16195265 by the same applicant, said document hereby being incorporated in its entirety by reference. However, even though this type of package is highly advantageous, many other types of packages may be used instead, having e.g. a tubular compartment, having peel opening(s), etc. As one example, a package as disclosed in U.S. Pat. No. 6,848,574, also by the same applicant and incorporated herein by reference, may be used.

The package disclosed in relation to the illustrative example has a rectangular, elongate shape. However, the package may also have other shapes, such as being of a square shape.

The catheter assembly as illustrated in FIGS. 1-4 comprises a catheter 1 having a hydrophilic surface, and preferably a hydrophilic surface coating, a small amount of wetting liquid 2 and a package 3 accommodating the catheter and the wetting fluid.

The catheter 1 may be any type of hydrophilic catheter, as is per se well known in the art. Preferably, the catheter comprises an enlarged rearward portion, e.g. forming a flared or frusto-conical connector 11, and an elongate shaft 12, connected to the connector 11, and in the opposite end having a catheter insertion end 13. Further, the catheter may also end directly at the end of the elongate shaft, without any connector, or be provided with other type of rearward arrangements.

At least a part of the elongate shaft 12 forms an insertable length to be inserted through a body opening of the user, such as the urethra in case of a urinary catheter. At least the insertable length is preferably, in the context of a hydrophilic catheter, provided with a hydrophilic surface, such as a hydrophilic surface coating, for example PVP, and which provides a low-friction surface when wetted with a wetting fluid. Typically, the insertable length is within 50-140 mm for a female patient and 200-350 mm for a male patient. Even though PVP is the preferred hydrophilic material, other hydrophilic materials may be used, such as hydrophilic polymers selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride.

However, a hydrophilic surface may also be realized in other ways, such as by forming the entire catheter, or part of the catheter, by a hydrophilic material, or by integrating a hydrophilic material in the catheter.

The hydrophilic surface is wetted when arranged in the package, and is maintained in a wetted, activated state during storage. The wetted hydrophilic surface is shown in grey in the figures.

The wetting fluid 2 is arranged directly in the compartment of the package which also houses the catheter, so that the hydrophilic surface of the catheter is in direct contact, i.e. in direct fluid communication, with the wetting liquid during storage.

The wetting liquid is preferably an aqueous liquid, such as water or saline. However, the wetting liquid may in addition comprise one or more additives.

The package is preferably made of sheet material. In the shown embodiment, the package is made of two sheet materials 31, connected around the edges to form an inner cavity housing the catheter and the optional wetting fluid. The first and second sheet materials are preferably connected around the edges by means of welding, forming welded edge joints. However, alternatively, a folded sheet material may also be used for forming the package, whereby one or several sides of the package may be closed by the fold instead of, or in addition to, the weld. The sheet material may also be provided in the form of a tube, requiring even less welded joints to close the package. However, depending on which sides that are closed, additional welds along the closed sides may still be required to form the tear lines, protrusions, etc, as discussed in the following.

The sheet material is preferably a tearable and/or peelable material, and preferably comprises a laminated sheet material, and preferably having a weldable inner layer and a protective outer layer.

Further, the package is preferably made of a material having low gas permeability, and preferably being entirely gas-impermeable.

The sheet materials are preferably of a flexible plastics material. The material may be transparent, but opaque or semi-opaque materials may also be used. For example, the sheets can be made of polymer materials such as polyethylene (PE), polypropylene (PP), polyamide (PA), poly(ethylene terephthalate) (PET), oriented polypropylene (OPP), oriented polyamide (OPA), etc. Also, the receptacle can be made of one or several materials functioning as barrier material or having low water vapor transmission. The material of the sheet material, or the material of one of the layers in case of a laminate, may to this end comprise or consist of one or several of aluminum, aluminum oxide, silicone oxide, metallocene polyvinylidene chloride (PVdC) and poly(ethylene-vinylalcohol) (EVOH). For example, the flexible material can be made as coextruded polyolefines with polyamides, poly(ethylene terephthalate) (PET), including barrier resins such as polyvinylidene chloride (PVdC) or poly (ethylene-vinylalcohol) (EVOH). However, other materials exhibiting similar properties are also feasible.

In the exemplary embodiment illustrated in the drawings, the package 3 is formed as an elongate package, comprising two longitudinal sides extending in a length direction of the package, and two short sides extending in a transversal direction of the package. All sides are closed, thereby forming a closed compartment accommodating the medical device in a sterile way. Preferably, the package is arranged to maintain sterility during a prolonged storage. The assembly preferably has a shelf life of at least 2 years, and most preferably at least 3 years, and even more preferably at least 5 years.

In the exemplary embodiment, the package is provided with tear openings for enabling opening of the package and extraction of the catheter. However, many other ways of opening the package are also feasible, such as peel openings, openable caps or lids, etc. It is also possible to combine various opening mechanisms in one package.

The longitudinal sides and short sides may be closed in various ways, such as by welded joints, by folding, etc. In the illustrative example, a first weld 34 is shown, arranged along one longitudinal side, and a second weld 35 is arranged along one short side.

Figure 1:
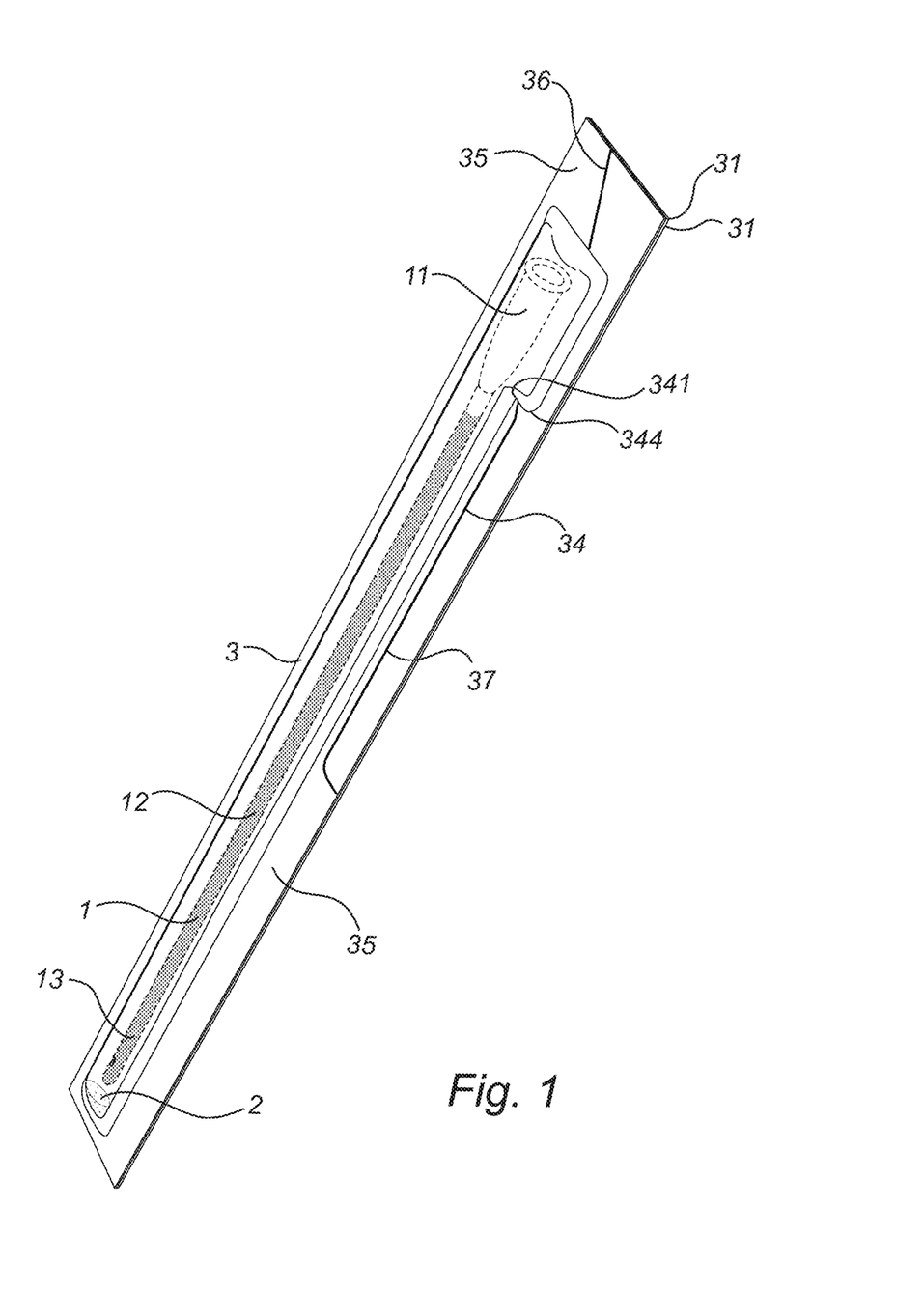
FIG. 1 is a perspective view of a medical device assembly in accordance with an embodiment of the present disclosure in a closed position.
Figures 2, 3:
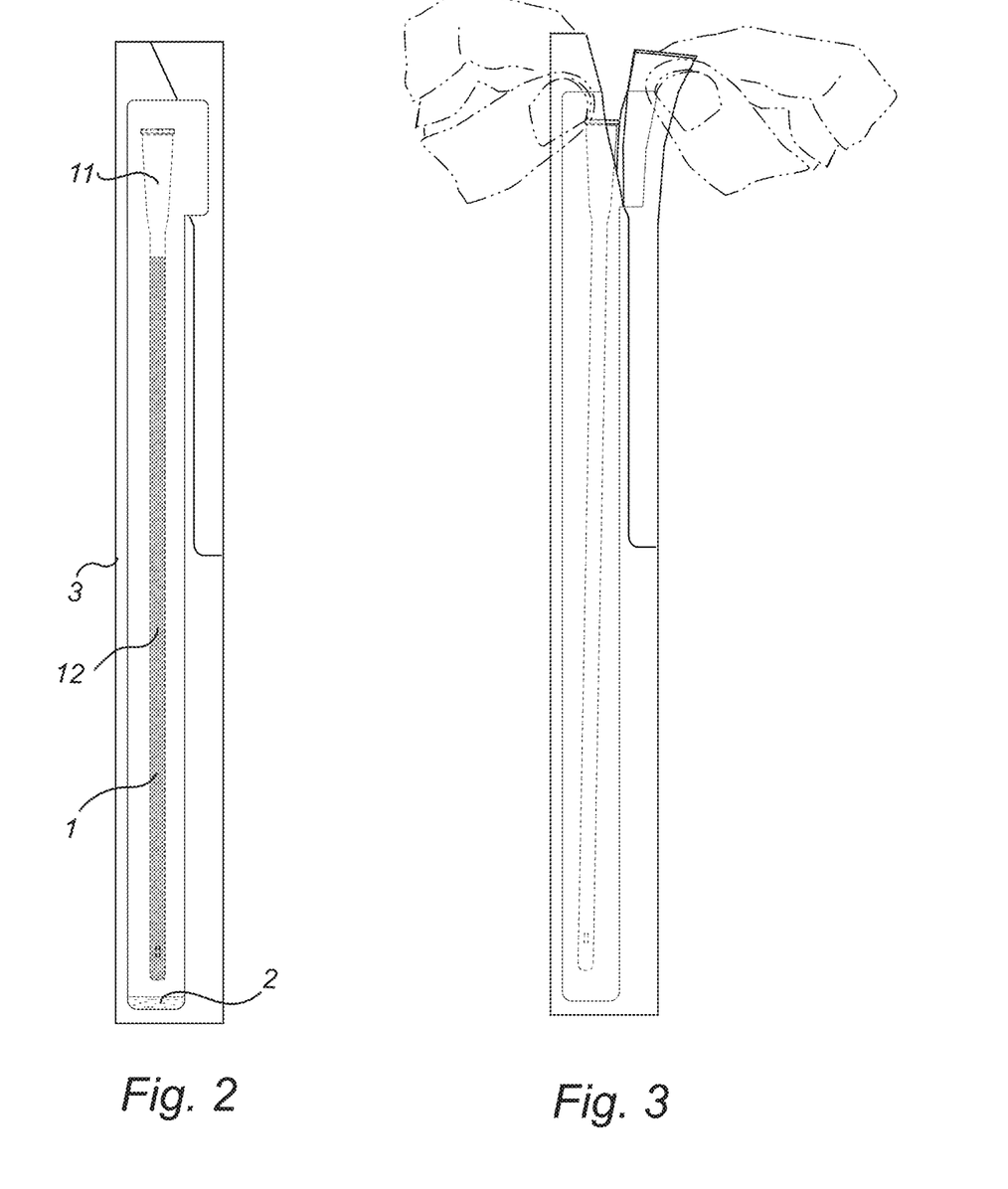
FIG. 2 is a top view of the medical device assembly of FIG. 1 in the same closed position.
FIG. 3 is a top view of the medical device assembly of FIG. 1 in a first opened position.
Figure 4:
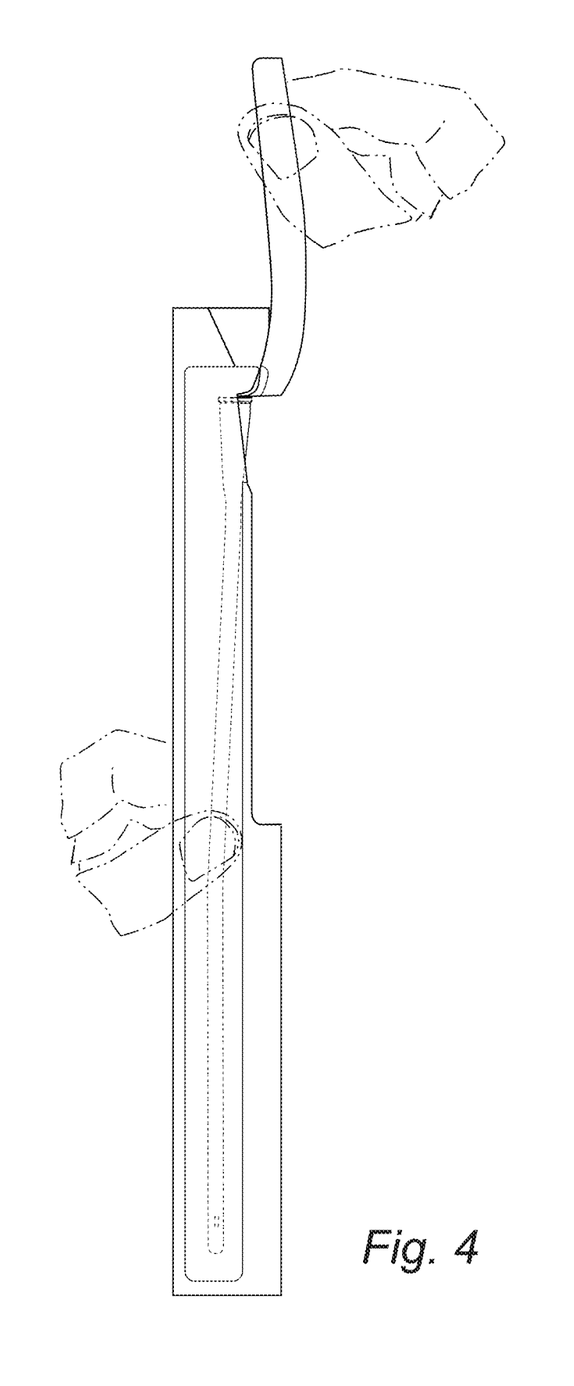
FIG. 4 is a top view of the medical device assembly of FIG. 1 in a second opened position.

In the illustrative example, two different tear openings are provided: A first tear line 36 and a second tear line 37. When opening the package with the first tear line 36, as illustrated in FIG. 3, the user grips the areas of the package arranged on both sides of the tear line 36, and pulls the gripping areas apart. Opening of the package with the second tear line 37 is illustrated in FIG. 4.

A method of manufacturing the above-discussed catheter assembly preferably comprises the following steps, performed in any order:
  Providing one or several sheet material(s);
  Forming the sheet material(s) to a package, e.g. by folding the sheet material or by arranging two or more sheets on top of each other;
  Providing a catheter having a hydrophilic surface on at least part thereof;
  Wetting the hydrophilic surface, e.g. by dipping the catheter in a wetting liquid;

Arranging the catheter in the package;
Arranging a small amount of additional wetting fluid within the package;
Closing and sealing the package; and
Sterilizing the package together with its content by steam sterilization.

Experimental Results

In some experimental tests to be discussed in the following, substrates made of the following substrate materials were used:

SA: Polyether block amid (PEBA)
SB: A polyolefin base polymer based on the commercially available polyolefin material Meliflex®.

The substrates were coated in accordance with a per se known hydrophilic coating process. In this coating process isocyanate was used to form a polyurea network for binding PVP.

The coated catheters were prepared for packing by dipping them in a wetting solution for 30 s, thereby wetting and activating the hydrophilic surface, and were subsequently packed in packages made of sheet material. The packages were generally rectangular in shape, and had the dimensions 460×40 mm. The nominal volume of the (single) compartments of the packages was approximately 140 ml. The wetted catheters were arranged in the packages together with a specified amount of the same wetting solution. Various wetting solution compositions and amounts of added wetting solution was tested, as presented in the following tables. The package material used was a gas-impermeable laminated sheet material of the type PET/Al/PP.

The closed packages, containing the wetted catheters and the small additional amount of wetting liquid, were then steam sterilized. The steam sterilization method used for these experiments was a so-called Steam-Air Mix process, which is generally used for sterilization of e.g. liquid filled syringes. In this process, the pressure in the autoclave/sterilization chamber is adjusted in dependence of the temperature, to avoid damage to the package. To this end, the temperature inside one package is measured with a sensor. From this temperature, the vaporization pressure of water is calculated (e.g. T=100 deg. C. gives a vapor pressure of 1.0 bar, and T=121 deg. C. gives a vapor pressure of 2.1 bar).

The pressure in the sterilization chamber was regulated continuously or regularly, such as every second, by introduction of compressed air, to adjust the external pressure inside the chamber to a pressure corresponding to the determined vapor pressure, and possibly with an additional support pressure preventing the packages from bursting. In these experiments, the support pressure was set to between 0.8 and 1.0 bar. The final sterilization temperature used was 121-123 deg. C., and the elevated sterilization temperature was maintained during a time period of 20 minutes.

The different wetting liquids used in the experimental tests were:
LA: 8.5% of weight of glycerol, 91.5% of weight of distilled water.
LB: 2.8% of weight of NaCl, 97.2% of weight of distilled water.
LC: 100% distilled water.

The test samples used are specified in Table 1 below:

TABLE 1

Specification of test samples

| Sample | Substrate | Wetting fluid | Support pressure sterilization [bar] | Temp. Sterilization [deg. C.] | Added volume of wetting liquid [ml] |
|---|---|---|---|---|---|
| Ex 1 | SA | LA | 1.0 | 121 | 0.3 |
| Ex 2 | SB | LA | 0.8 | 123 | 0.3 |
| Ex 3 | SB | LA | 0.8 | 123 | 10 |
| Ex 4 | SA | LA | 0.8 | 123 | 0.3 |
| Ex 5 | SA | LB | 0.8 | 123 | 0.3 |
| Ex 6 | SB | LA | 0.8 | 121 | 0 |
| Ex 7 | SB | LA | 0.8 | 121 | 1 |
| Ex 8 | SB | LA | 0.8 | 121 | 2 |
| Ex 9 | SB | LB | 0.8 | 121 | 0 |
| Ex 10 | SB | LB | 0.8 | 121 | 1 |
| Ex 11 | SB | LB | 0.8 | 121 | 2 |
| Ex 12 | SB | LC | 0.8 | 121 | 2 |

Notably, Ex 6 and Ex 9 are included as comparative examples. As a further comparative example, Ex 13, a catheter with substrate SB was used, together with wetting liquid LA, in an amount of 0.3 ml. This package was, however, not steam sterilized. Instead, it was sterilized with E-beam sterilization, at 56 kGy.

In a first test, the relative slipperiness and roughness of the catheters were evaluated. To this end, the catheters were extracted from the packages, and the slipperiness and roughness were evaluated manually, and determined to be somewhere on a scale from 0-9, where 0 corresponds to very low slipperiness and high roughness, and 9 corresponds to very high slipperiness and very low roughness. The results of this first test are presented in Table 2 below.

TABLE 2

Result of evaluation of slipperiness and roughness

| Sample | Slipperiness | Roughness |
|---|---|---|
| Ex 1 | 9 | 9 |
| Ex 2 | 8 | 8 |
| Ex 4 | 9 | 7-8 |
| Ex 5 | 8-9 | 7-8 |
| Ex 13 | 6-7 | 9 |

It has been empirically found by the applicant that slipperiness and roughness values equal to or exceeding 7 are good and fully acceptable catheters. Thus, it is noted that all the tested examples steam sterilized in accordance with the present disclosure, i.e. Ex 1, Ex 2, Ex 4 and Ex 5, performed very good in this test, all having slipperiness and roughness values above or much above the lower limit of 7, and at least as good as the E-beam sterilized catheters of Ex 13.

In a second test, the friction of the wetted hydrophilic surface for three of the examples was tested. To this end, the catheters were removed from the packages and allowed to dry in air for 3 minutes. Thereafter, the friction was tested using a Harland FTS Friction Tester, available from Harland Medical Systems, with a clamp force of 300 g and a pull speed of 1.0 cm/s. The results of this second test are presented in Table 3 below.

TABLE 3

| Result of friction measurement | |
|---|---|
| Sample | Coefficient of friction |
| Ex 1 | 0.034 |
| Ex 4 | 0.045 |
| Ex 5 | 0.043 |

It has been empirically found by the applicant that a friction coefficient equal to or below 0.1 is sufficient to obtain fully acceptable catheters. Thus, it is noted that the friction of the catheters in Ex 1, Ex 4 and Ex 5 which were tested are much below this upper limit.

In a third test, water retention was analyzed. For conventional dry catheters, it is common to analyze water retention by first weighing the catheters when dry, and thereafter, after having wetted the catheters, determining the weight of the wetting liquid maintained in the hydrophilic coating after various time periods, such as after 0 s, 30 s, 1 minutes, 5 minutes, etc. However, in the here tested examples, the catheters were already wetted when extracted from the packages. Thus, a reversed water retention method was used. Thus, after having been extracted from the packages, the wet weights of the catheters were measured 1 minute and 3 minutes after extraction. The catheters were then allowed to dry in air until constant weight is achieved and the dry weight is measured. The amount of water present in the coating that has evaporated is then calculated as water retention (mg/cm2) based on the difference between the wet weights and the dry weight. The results of this third test are presented in Table 4 below.

TABLE 4

| Result of reversed water retention measurement | | |
|---|---|---|
| Sample | Water retention after 1 minute [mg/cm$^2$] | Water retention after 3 minutes [mg/cm$^2$] |
| Ex 1 | 11.7 | 10.8 |
| Ex 4 | 11.9 | 11.0 |
| Ex 5 | 10.4 | 9.7 |

These water retention values are comparable to the water of commercially available hydrophilic catheter, such as the LoFric® catheter produced by the present Applicant. Commercially available catheters typically have water retention values after 1 minute of about 8-12 mg/cm2, and after 3 minutes of about 6-10 mg/cm2. Thus, the water retention of all the tested catheters is sufficient to obtain fully acceptable catheters. Notably, a urinary catheter for intermittent use is typically only used for some minutes.

In a fourth test, it was evaluated whether the catheter produces were adequately sterilized or not. To this end, spore threads as indicators of sterility were prepared. Specifically, spore threads with 106 spores of Bacillus stearothermophilus was used to control the sterility of the products. Two threads were placed in each package to be evaluated; one on the outside of the catheter and one inside the catheter tube. After having been subject to the above-discussed steam sterilization, the packages prepared with spore threads were delivered to a laboratory for bacterial growth.

In this fourth test, the catheter products of Ex 2-Ex 12 were analyzed. It was found that there was no bacterial growth in any of the catheter products of Ex 2-Ex 5 and Ex 7-Ex 12. However, in Ex 6, which did not contain any additional wetting liquid, some bacterial growth occurred in the spore thread that was placed inside the lumen of the catheter. This indicates that provision of an amount of additional wetting liquid inside the catheter package ensures that the packages are completely sterile after having been steam-sterilized, even if this amount of additional wetting liquid is extremely small, such as only 0.3 ml as in Ex 2, Ex 4 and Ex 5. However, without any such additional amount of wetting liquid, such as in Ex 6, steam sterilization may not be sufficient to obtain complete sterility. It is thus concluded that in order to ensure that complete sterility is obtained when using steam sterilization, a small amount of additional wetting liquid is necessary.

Specific embodiments of the invention have now been described. However, several alternatives are possible, as would be apparent for someone skilled in the art. For example, the volume of additional wetting liquid appears not to be critical for rendering steam sterilization possible, as long as a sufficiently humid atmosphere is obtained inside the package. Further, even though the above embodiments primarily focus on urinary catheters, other medical devices can also be packed and sterilized in the same way. Further, the hydrophilic surface may be in the form of a coating, but may also be provided in other ways, and the hydrophilic surface may be arranged on an external surface of the medical device, on an internal surface of the device, such as in a lumen, and may cover the whole medical device or only part(s) thereof. Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the subject description, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A sterilized medical device assembly, comprising:
a medical device having a hydrophilic surface on at least a part thereof;
a package forming a closed compartment accommodating said medical device, wherein said medical device is arranged in an activated state in said package with said hydrophilic surface being wetted with a wetting fluid; and
a wetting liquid being freely arranged in said closed compartment of the package, and in direct contact with said hydrophilic surface of the medical device;
wherein a volume of said wetting liquid corresponds to between 0.01% and 10% of a volume of said closed compartment, and wherein said medical device assembly is steam sterilized.

2. The sterilized medical device assembly of claim 1, wherein the volume of said wetting liquid corresponds to between 0.1% and 5% of the volume of said closed compartment.

3. The sterilized medical device assembly of claim 1, wherein the volume of said wetting liquid is in the range 0.1-5 ml.

4. The sterilized medical device assembly of claim 1, wherein the volume of said wetting liquid is in the range 0.2-3 ml.

5. The sterilized medical device assembly of claim 1, wherein the package is impermeable to the wetting liquid.

6. The sterilized medical device assembly of claim 1, wherein the package comprises a laminated sheet material, having a weldable inner layer and a protective outer layer.

7. The sterilized medical device assembly of claim 1, wherein the package comprises one or several material(s) having a melting temperature exceeding 120 deg. C., whereby the package can endure temperatures of 120 degrees Celsius or higher without significant deformation or deterioration.

8. The sterilized medical device assembly of claim 1, wherein the medical device comprises one or several material(s) having a melting temperature exceeding 120 deg. C., whereby the medical device can endure temperatures of 120 degrees Celsius or higher without significant deformation or deterioration.

9. The sterilized medical device assembly of claim 1, wherein the medical device is a catheter.

10. The sterilized medical device assembly of claim 1, wherein the medical device is a urinary catheter.

11. The sterilized medical device assembly of claim 1, wherein the medical device is a urinary catheter for intermittent use.

12. The sterilized medical device assembly of claim 1, wherein the wetting liquid is an aqueous liquid, comprising at least 75% by weight of water.

13. The sterilized medical device assembly of claim 12, wherein the wetting liquid comprises at least 90% by weight of water.

14. The sterilized medical device assembly of claim 1, wherein the wetting liquid is an aqueous liquid comprising water and at least one additive.

15. The sterilized medical device assembly of claim 12, wherein the wetting liquid is an aqueous liquid comprising water and at least one additive.

16. The sterilized medical device assembly of claim 14, wherein the at least one additive comprises at least one osmolality increasing agent.

17. The sterilized medical device assembly of claim 16, wherein the osmolality-increasing agent is selected from the group consisting of glucose, glycerol, sorbitol, sodium chloride, sodium citrate; sodium benzoate; calcium chloride, potassium chloride, potassium iodide and potassium nitrate.

18. The sterilized medical device assembly of claim 1, wherein the medical device is a catheter that comprises a substrate and a hydrophilic coating, wherein the substrate comprises at least one of the following material: a polyurethane, a polyether block amide, silicon rubber, an elastomeric alloy, a polyolefin alloy based on polypropylene or SEBS (Styrene Ethylene Butadiene Styrene), Santoprene, or mixtures thereof.

19. A method for producing a sterilized medical device assembly, comprising:
   providing a medical device having a hydrophilic surface on at least a part thereof;
   wetting the hydrophilic surface of the medical device with a wetting fluid;
   accommodating the medical device in a closed and sealed compartment of a package together with a wetting liquid being freely arranged in the closed compartment and in direct contact with said hydrophilic surface of the medical device, wherein a volume of said wetting liquid corresponds to between 0.01% and 10% of a volume of said closed compartment; and
   steam sterilizing said medical device assembly.

20. The method for producing a sterilized medical device of claim 19 wherein all parts of the medical device assembly are capable of enduring a temperature of at least 100 deg. C. without degradation.

21. The method for producing a sterilized medical device of claim 19 wherein all parts of the medical device assembly are capable of enduring a temperature of at least 120 deg. C. without degradation.

22. A sterilized urinary catheter assembly, comprising:
   a urinary catheter having a hydrophilic surface on at least a part thereof;
   a package forming a closed compartment accommodating said urinary catheter, wherein said urinary catheter is arranged in an activated state in said package with said hydrophilic surface being wetted with a wetting fluid; and
   a wetting liquid being freely arranged in said closed compartment of the package, and in direct contact with said hydrophilic surface of the urinary catheter;
   wherein a volume of said wetting liquid corresponds to between 0.01% and 5% of a volume of said closed compartment, wherein all parts of the urinary catheter assembly are capable of enduring a temperature of at least 100 deg. C. without degradation, and wherein said urinary catheter assembly is steam sterilized.

* * * * *